United States Patent
Burwell et al.

(10) Patent No.: US 6,889,865 B1
(45) Date of Patent: May 10, 2005

(54) METHOD AND APPARATUS FOR PRESSURE TESTING STORAGE TANKS

(75) Inventors: John Burwell, Eagan, MN (US); Don Abel, Bettendorf, IA (US); Chester Batzkiel, Tipton, IA (US); Greg Carty, Clarence, IA (US); Onesimo Gomez, Norwalk, CA (US); David Lehman, Tipton, IA (US); Roberto Sanchez, Corona, CA (US); Robin L. Berg, Sr., Hudson, WI (US)

(73) Assignee: Xerxes Corporation, Minneapolis, MN (US)

( * ) Notice: Subject to any disclaimer, the term of this patent is extended or adjusted under 35 U.S.C. 154(b) by 33 days.

(21) Appl. No.: 09/617,239

(22) Filed: Jul. 14, 2000

Related U.S. Application Data

(60) Provisional application No. 60/216,687, filed on Jul. 7, 2000.

(51) Int. Cl.[7] ............................................. B65D 88/76
(52) U.S. Cl. .............................. 220/567.1; 220/567.2; 220/359.1
(58) Field of Search ................................ 220/610–614, 220/319, 359.1, 378, 320, 359.4, 567.1, 567.2; 285/293.1, 294.2, 294.4; 215/258, 257; 73/49.8, 73/49.3, 49.2; 156/289, 304.5, 383, 304.3; 29/423; 52/192; 138/89.4, 89.1, 89, 96 R

(56) References Cited

U.S. PATENT DOCUMENTS

| | | | | |
|---|---|---|---|---|
| 495,775 A | * | 4/1893 | Bonnamy | 215/275 |
| 1,335,233 A | * | 3/1920 | Hammer | 220/320 |
| 2,893,590 A | * | 7/1959 | Buckley | 220/304 |

(Continued)

Primary Examiner—Joseph C. Merek
(74) Attorney, Agent, or Firm—Steven B. Kelber; DLA Piper Rudnick Gray Cary US LLP

(57) ABSTRACT

A storage tank includes a dome placed over an open end of a riser and secured to the riser by a fiberglass ring formed over a flanged end of the dome and a portion of the riser that is adjacent to the dome such that the interior of the tank may be pressurized to facilitate leak detection. A fillet of putty or other material that will not adhere or only weakly adhere to the riser and dome is placed over a horizontal surface of the flanged end. This arrangement allows the dome to be removed from the riser by simply grinding away a corner portion of the fiberglass ring at the bottom edge of the dome. The dome may then be reused for other tanks.

In another embodiment, a domed cover is formed on an interior of the riser. The domed cover preferably includes a flat outside edge which is permanently attached to the inside wall of the riser. After the tank has been installed and tested, the domed portion is cut away, leaving the flat edge attached to the interior wall of the riser. The flat edge then serves as a flange for supporting a required pump, filter or other device.

28 Claims, 4 Drawing Sheets

U.S. PATENT DOCUMENTS

| | | | | |
|---|---|---|---|---|
| 3,036,728 A | * | 5/1962 | Gibb | 220/680 |
| 3,241,701 A | * | 3/1966 | Boggs | 220/4.13 |
| 3,334,776 A | * | 8/1967 | Ellis | 220/260 |
| 3,344,945 A | * | 10/1967 | Bozek | 220/319 |
| 3,685,682 A | * | 8/1972 | Frey, III | 220/359.1 |
| 3,748,816 A | * | 7/1973 | Asmus | 53/420 |
| 3,825,148 A | * | 7/1974 | Hunter et al. | 220/359.1 |
| 3,920,254 A | * | 11/1975 | Johnston et al. | 277/462 |
| 4,046,306 A | * | 9/1977 | Cass | 229/5.7 |
| RE29,636 E | * | 5/1978 | Gilbu | 52/20 |
| 4,112,644 A | * | 9/1978 | Allen | 52/245 |
| 4,335,757 A | * | 6/1982 | Lankston | 138/92 |
| 4,562,934 A | * | 1/1986 | Hammond | 220/685 |
| 4,609,213 A | * | 9/1986 | Tonchen | 285/419 |
| 5,096,206 A | * | 3/1992 | Andre et al. | 277/314 |
| 5,123,679 A | * | 6/1992 | Twerdochlib | 285/114 |
| 5,295,391 A | * | 3/1994 | Mastandrea et al. | 73/49.2 |
| 5,527,070 A | * | 6/1996 | Blackwell | 285/45 |
| 5,531,485 A | * | 7/1996 | House et al. | 285/230 |
| 5,582,318 A | * | 12/1996 | Dietrich | 220/319 |
| 5,908,211 A | * | 6/1999 | Blackwell et al. | 285/294.2 |
| 6,530,575 B2 | * | 3/2003 | Poquet et al. | 277/592 |

* cited by examiner

METHOD AND APPARATUS FOR PRESSURE TESTING STORAGE TANKS

This application claims the benefit from Provisional Application Ser. No. 60/216,687 filed Jul. 7, 2000, entitled METHOD AND APPARATUS FOR PRESSURE TESTING STORAGE TANKS. The entirety of that provisional application is incorporated herein by reference.

BACKGROUND OF THE INVENTION

1. Field of the Invention

The invention relates to pressure testing storage tanks generally, and more particularly to a method and apparatus that can be used for pressure testing storage tanks that are normally not sealed.

2. Discussion of the Background

Storage tanks in general, and underground storage tanks in particular, are used to store a wide variety of materials. In some applications, the nature of the material dictates that the tank be sealed under normal conditions. In these applications, there are normally governmental requirements for leak testing the tanks. The leak testing is typically accomplished by sealing the tank using the sealing mechanism provided by the tank (and capping off any pipes or connecting fittings installed in the tank), pressurizing the tank, and detecting any escaping air by applying soapy water to the exterior of the tank and looking for bubbles caused by air escaping from the pressurized interior of the tank.

In other applications, such as wastewater tanks, the storage tanks are not normally sealed. Such tanks typically include an open riser that provides access to the tanks from aboveground. Furthermore, because of nature of the material to be stored in such tanks, there are typically no government requirements to perform leak detection tests on these tanks. However, it is still desirable to ensure that such tanks are watertight even if there are no governmental requirements for leak detection.

What is needed is an inexpensive method and apparatus for leak testing tanks that are not normally sealed.

SUMMARY OF THE INVENTION

The present invention meets the aforementioned need to a great extent by providing a method and apparatus for sealing a normally open riser to facilitate a pressurized leak detection test. In one embodiment, a dome is placed over an open end of the riser and is secured to the riser by a fiberglass ring formed over a flanged end of the dome that extends over the top of the riser and a portion of the riser that is adjacent to the fiberglass dome such that the interior of the tank may be pressurized to facilitate leak detection. A fillet of putty or other material that will not adhere, or only weakly adhere, to the riser and dome is placed over an exposed end of the dome that is perpendicular to the riser. This arrangement allows the dome to be removed from the riser by simply grinding away a corner portion of the fiberglass ring at the bottom edge of the dome. The dome may then be reused for other tanks, thereby saving money.

In a second embodiment, which is particularly well suited to applications in which a pump, filter or other device must be installed in the riser, a domed cover is formed on an interior of the riser. The domed cover preferably includes a flat outside edge which is permanently attached to the inside wall of the riser. After the tank has been installed and tested, the domed portion is cut away, leaving the flat edge attached to the interior wall of the riser. The flat edge then serves as a flange for supporting the required pump, filter or other device.

BRIEF DESCRIPTION OF THE DRAWINGS

A more complete appreciation of the invention and many of the attendant features and advantages thereof will be readily obtained as the same become better understood by reference to the following detailed description when considered in connection with the accompanying drawings, wherein.

DETAILED DESCRIPTION OF THE PREFERRED EMBODIMENTS

The present invention will be discussed with reference to preferred embodiments of pressurizable storage tanks. Specific details, such as dimensions of various portions of the tanks, are set forth in order to provide a thorough understanding of the present invention. The preferred embodiments discussed herein should not be understood to limit the invention.

Figure 1:
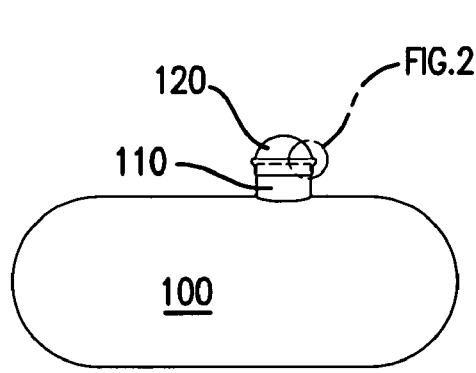
FIG. 1 is a side view of a storage tank with a dome covering a riser according to a first embodiment of the present invention.

Referring now to the drawings, wherein like reference numerals designate identical or corresponding parts throughout the several views, FIG. 1 shows a side view of a storage tank 100 including a riser 110 and a riser sealing dome 120. The tank 100, the riser 110 and the dome 120 may be made from a variety of materials, but preferably are constructed of fiber reinforced plastic, which is referred to herein as fiberglass. The riser 110 is present to provide access to the interior of the tank 100. Risers (as used herein, the term riser includes what are referred to in the art as manways) are typically 18–36 inches in diameter and typically have a circular circumferential shape. However, those of skill in the art will recognize that other shapes, including oval and even polygonal, are possible. Hence, as used herein, 'dome' and 'domed' refer to a structure with a central raised portion regardless of the circumferential shape of the structure.

Figure 2:
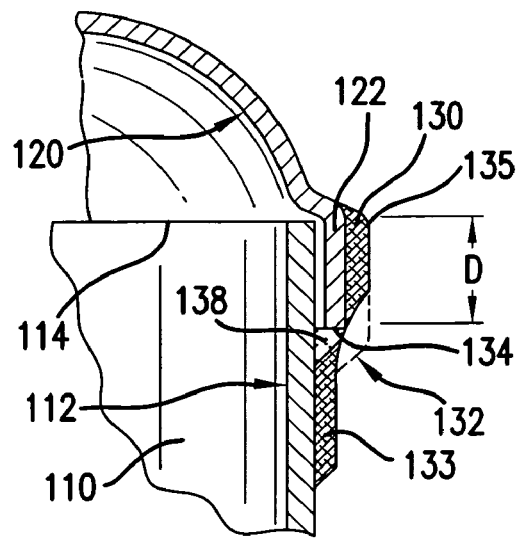
FIG. 2 is a cross sectional view of a portion of the tank of FIG. 1 showing the connection between the dome and riser.
Figure 3:
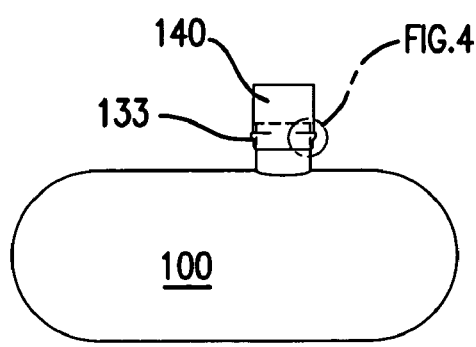
FIG. 3 is a side view of the storage tank of FIG. 1 showing an installation of an optional riser extension.

FIG. 2 illustrates a portion of the riser 110 and dome 120 where the two are joined. The dome 120 has a flared end 122 sized to accept the upper end 114 of the riser 110. The length of the flared end 122 is preferably approximately four inches. A fillet 138 covers the horizontal surface 134 of the flared end 122 of the dome 120 and a portion of the of the vertical wall 112 of the riser 110 not covered by the horizontal surface 134. The fillet 134 preferably comprises a putty. The fillet 134 may also be a hollow spacer formed by a material, such as cardboard, that will easily tear when pulled by a human being of ordinary strength. The fillet 134 has an exposed surface that preferably forms an angle of approximately 45 degrees with respect to the vertical wall 112 of the riser 110. The fillet 134 preferably will not bond or only weakly bond to both the vertical wall 112 and the flared end 122 of the dome 120.

A structural band 130 is formed over the flared end 122, the fillet 134 and a portion of the vertical wall 112 of the riser 110. The band 130 includes material in the portion 132 illustrated with dashed lines in FIG. 2. The band 130 is preferably formed of fiberglass, although any structural adhesive material which can be easily cut may be used. The band 130 is adhered to the flared end 122 of the dome 120 and to the vertical wall 112 of the riser 110, but is preferably not adhered to the fillet 138. The structural band 130 forms an airtight seal between the dome 120 and the riser 110. This airtight seal (assuming any other openings are closed off) allows the tank 100 to be pressure tested. The band 130 is preferably of sufficient strength such that testing at a pressure of 25 p.s.i. may be performed. (In practice, production tanks are normally tested at 3–5 p.s.i. even though they may be capable of being pressurized to 25 p.s.i. or more. The only requirement for the airtight seal in the present invention is that the seal be capable of withstanding pressures or vacuums of sufficient strength to detect leaks in the tank). The testing is preferably performed on at least three occasions: when the tank 100 is about to leave the factory, when the tank 100 has been shipped and arrived at its destination but before any excavation has begun, and when the tank has placed in a hole but before backfilling has begun. Testing may also be performed while the tank is being backfill as long as the riser remains accessible.

When all desired testing has been completed, the dome 120 is ready for removal from the riser 110. This is easily accomplished due to the presence of the fillet 138. In preferred embodiments, a grinder is used to grind through a portion 132 of the band 130 to expose an edge of the flared end 122 of the dome 120. In order to aid an operator of the grinder to spot the flared end 122, the band 130 and flared end 122 are preferably colored differently. The grinding operation is performed all along the circumference of the riser 110. Because there is no adhesive between the dome 120 and the riser 110 save for the structural band 130, and because the fillet 138 is not adhered to the dome 120 and/or the riser 110, the dome 120 may be removed from the riser 110 at this point.

Figure 4:
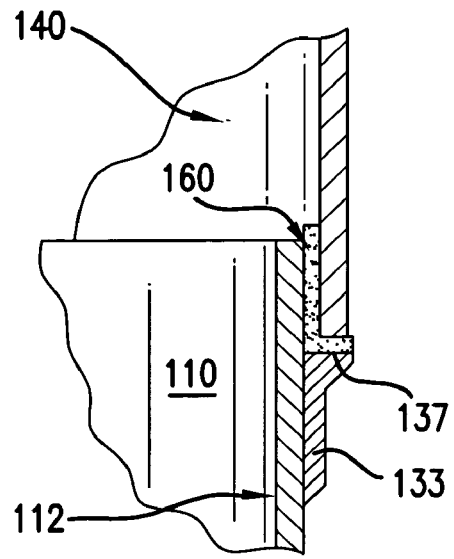
FIG. 4 is a cross sectional view showing the connection between the optional riser extension and the riser of the storage tank of FIG. 3.

After removal of the dome 120, a portion 133 of the band 130 and the fillet 138 remain on the riser 110. As shown in FIG. 4, this portion 133 may be used as a support and positioning aid in the event that installation of a riser extension 140 is necessary. In this event, the portion 133 is preferably further ground to produce a flat surface 137 on which the riser extension may be placed, as shown in FIG. 4. Depending upon how far down the portion 133 is ground, a portion of the fillet may or may not be left at the conclusion of the grinding process. The riser extension 140 is adhered to the riser 110 by adhesive 160.

The embodiment discussed above has several important advantages. First, the manner in which the dome 120 is attached and removed from to the riser 110 allows the dome 120 to be returned to the factory and reused on later tanks. It is recognized that it may not even be necessary to remove the remainder 135 of the band 130 from the dome 120 as subsequent bands 130 may simply be formed on top of the remainder 135. Second, because the dome 120 is securely attached to the riser 110 as the tank 100 leaves the factory, the end of the riser 110 not attached to the tank 100 is protected from damage during shipping. Third, as discussed above, the remainder 133 of the band 130 aids in the installation of a riser extension 140. Fourth, the provision of the dome over the riser ensures that no water will collect in the riser or tank. This is important in cold weather locations where freezing water may cause damage.

Figure 5:
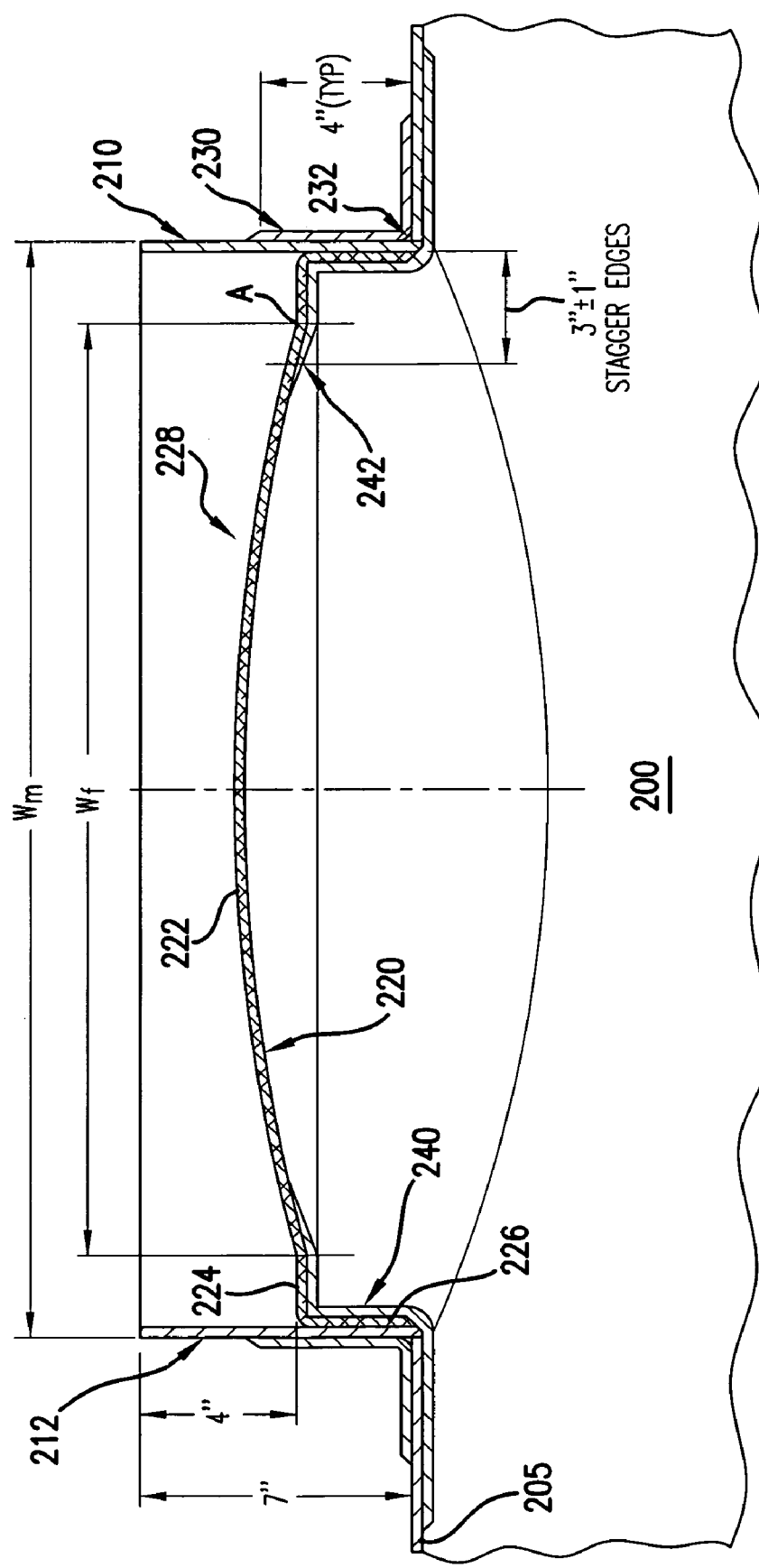
FIG. 5 is a cross sectional view of a portion of storage tank having a riser with an internal domed cover according to a second embodiment of the present invention.

FIG. 5 is a cross sectional view of a portion of a tank 200 with a riser 210 having an internal sealing dome 220 according to a second embodiment of the present invention. The riser 210 is attached to the cylindrical tank wall 205. Reinforcing members 230 are present at intervals around the riser 210. A fillet of putty 232 is preferably provided to ensure that the reinforcing members 230 do not become creased. The sealing dome 220 includes a vertical wall 226 that is in a close spatial relationship, and preferably attached, to the riser wall 212. The sealing dome 220 also includes a top 228 that includes a flat portion 224 and a domed portion 222.

The sealing dome 220 is also supported by a fiberglass retainer 240. The fiberglass retainer 240 extends from the inside surface of the tank wall 205, up along the dome vertical wall 226, underneath the flat portion 224 and ends in a tapered section 242 that extends underneath the domed portion 222. The retainer 240 provides support for the dome 220 in addition to the bond between the vertical dome wall 225 and the riser wall 212.

Figure 6:
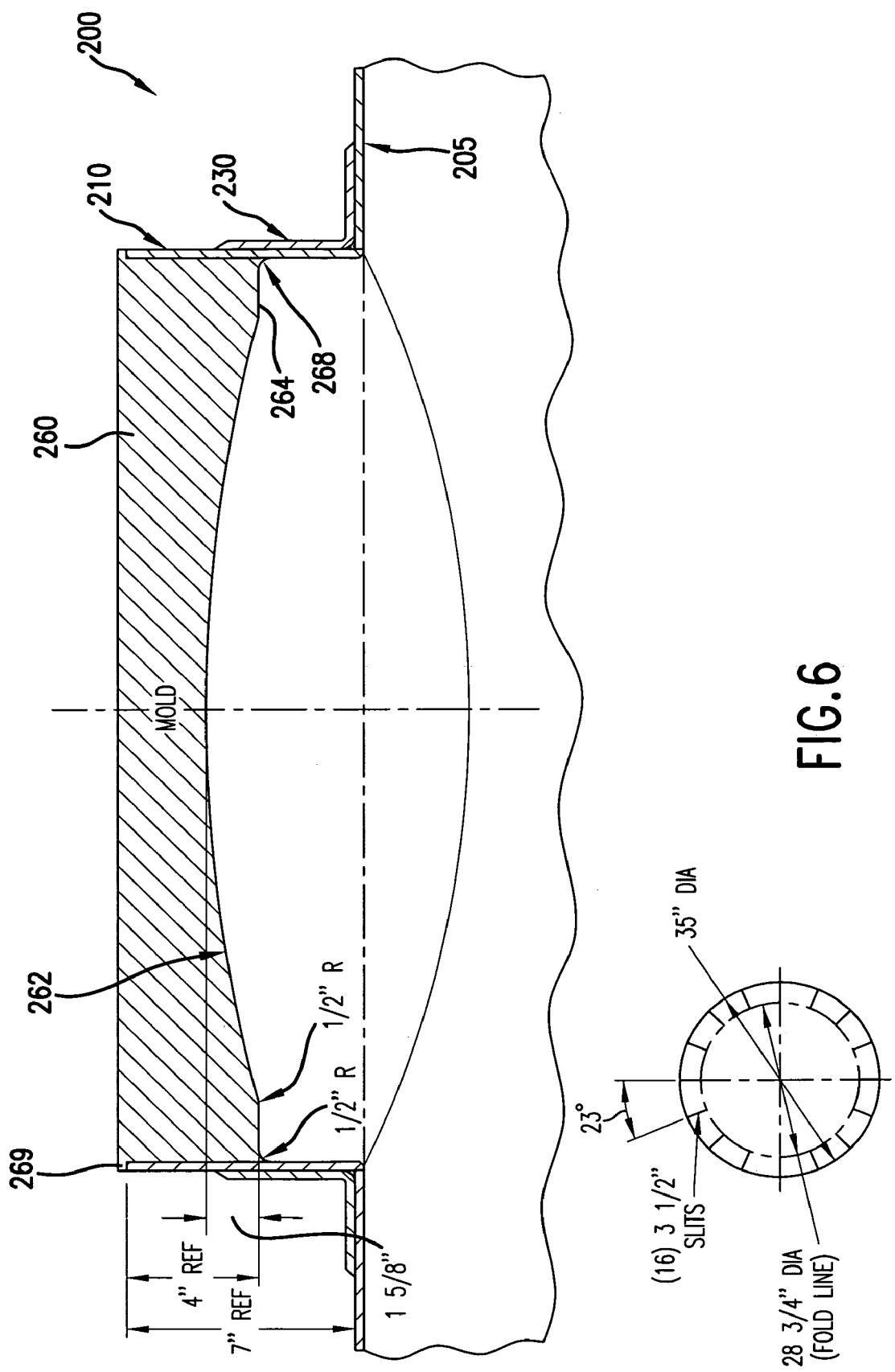
FIG. 6 is a cross sectional view of the portion of the storage tank of FIG. 5 during an intermediate stage in construction.

FIG. 6 shows how the dome 220 is manufactured. A tank 200 has been manufactured in halves in a conventional manner. The halves have not yet been joined. A riser 210 and reinforcing members 230 have been installed in one of the tank 200 halves, again in a conventional manner. The inside surface of the riser wall 212 has been abraded in preparation for the formation of a fiberglass bond. At this point, a mold 260 is inserted into the riser 210. The mold 260 includes a domed surface 262 (corresponding to domed portion 222) at the center and a flat surface 264 (corresponding to flat portion 224) at its periphery. The mold 260 also includes a rounded edge 268 at its outermost portion, which prevents creases to material to be applied over the mold 260.

The mold 260 is held in the riser 210 by the top flanges 269 which extend over the top of riser wall 212. With the mold 260 installed, fiberglass is layed up over the mold 260 to form the dome 220. The fiberglass retainer 240 is then formed, which can occur either before or after the mold 260 is removed. After the fiberglass retainer 240 is formed, the tank halves may be joined together and the tank completed in a conventional manner.

Rather than inserting a mold 260 into the riser 210, it is also possible to use the mold 260 outside of the tank 200 to create a corresponding thin fiberglass skin of, for example, a 1/16 inch thickness. This skin could then be placed in the riser 260 and subsequent layers of fiberglass could be layed up over the skin in the same manner as they are layed up over the mold 260.

Figure 7:
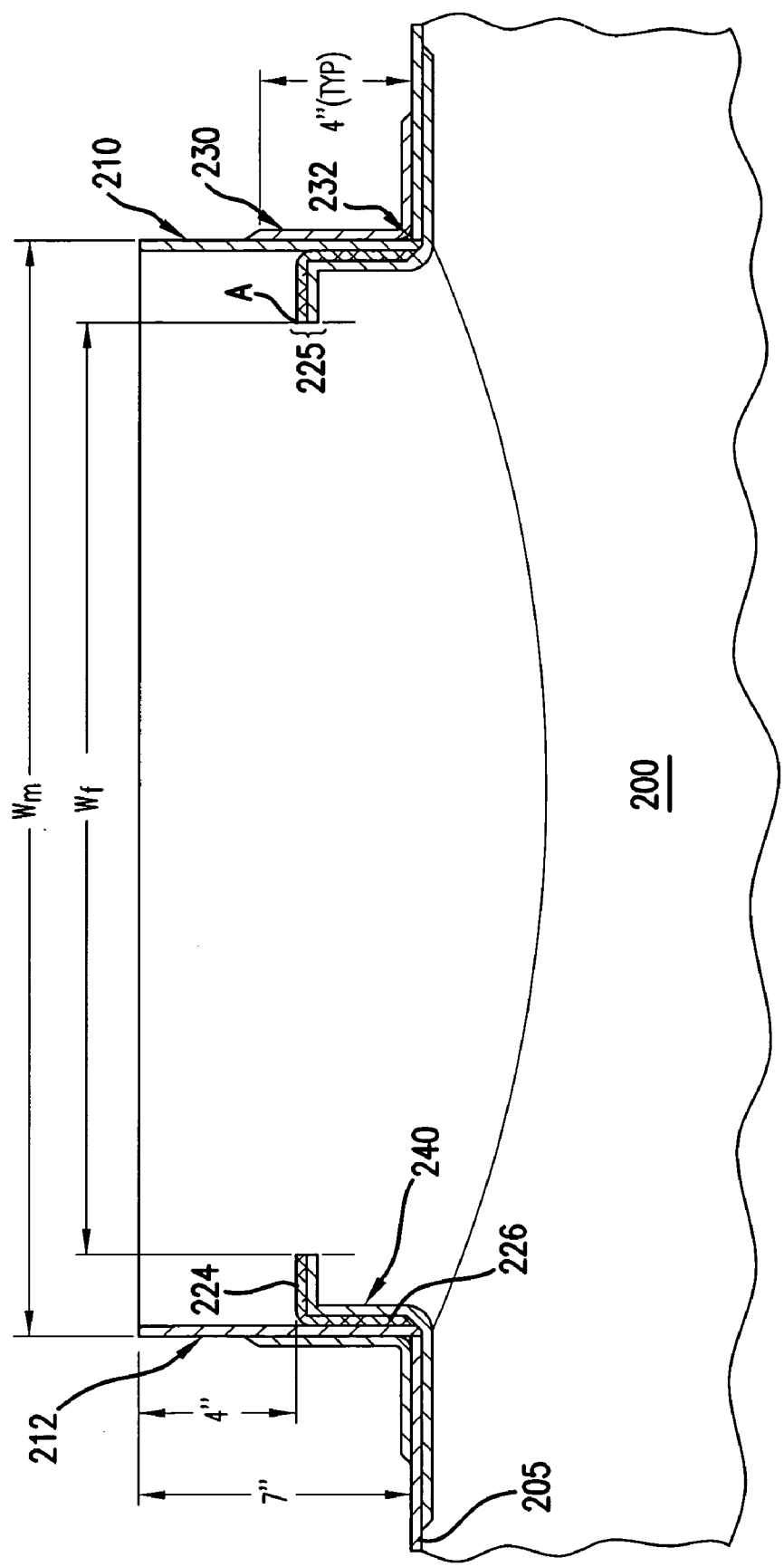
FIG. 7 is a cross sectional view of the storage tank of FIG. 5 with the central dome portion removed.

With the dome 220 installed, and any other openings properly sealed off, the tank 200 may be pressure tested to 25 p.s.i or more. After all required pressure testing is complete, the dome 220 is cut to provide access to the tank 200 through the riser 210. Referring back now to FIG. 5, the dome 220 may be cut at the point A which indicates the joint between the domed portion 222 and the flat portion 224. Cutting the dome 220 at point A will result in a flange 225 (formed by flat portion 224) being left behind as shown in FIG. 7. The flange 225 may be used to support a pump or filter in the riser 210. The dome 220 may be cut at other locations if a flange of a different width is desired.

An important advantage of this embodiment is that the dome 220 may be installed without adding to the overall height of the tank 200. This can be an important advantage when shipping costs are considered. Also, because the portion of the dome 220 that is cut out is not reused, it is not necessary to return it to the factory.

In any of the embodiments discussed above, it is preferable that the tank be allowed to "breathe" when not being pressure tested. Thus, if the tank has no openings to the interior chamber, it is desirable to include a valve on the dome such that the valve can be opened when no pressure testing is being performed. This same valve could be used as the means to pressurize the interior of the tank.

Obviously, numerous modifications and variations of the present invention are possible in light of the above teachings. It is therefore to be understood that within the scope of the appended claims, the invention may be practiced otherwise than as specifically described herein.

What is claimed is:

1. A storage tank comprising:
   a main body;
   a riser attached to the main body;
   a sealing dome covering an end of the riser, the sealing dome and the riser forming an overlapping joint;
   a circumferential fillet covering the joint, the fillet having a first surface adjacent to a portion of the sealing dome and a second surface adjacent to a portion of an exterior wall of the riser, the fillet not adhering to the portion of the sealing dome and the portion of the riser; and
   a sealing band formed over the fillet, the sealing band being attached to the sealing dome and to the riser and forming an airtight seal between the riser and the sealing dome; the sealing band being comprised of fiberglass.

2. The storage tank of claim 1, wherein the sealing dome includes a flanged end sized to accept the riser and wherein the sealing dome is positioned with the flanged end over a top end of the riser.

3. The storage tank of claim 2, wherein the first surface of the fillet is adjacent to an edge of the flanged end of the sealing dome and the fillet has a third surface connected to the first surface and the second surface.

4. The storage tank of claim 3, wherein an angle formed between the third surface and the riser walls is approximately forty five degrees.

5. The storage tank of claim 1, wherein the riser is comprised of fiberglass.

6. The storage tank of claim 1, wherein the sealing dome is comprised of fiberglass.

7. The storage tank of claim 1, wherein the sealing dome comprises a vertical wall and a top attached to an inside surface of the vertical wall.

8. The storage tank of claim 7, wherein the top includes a flat outer portion and a domed inner portion.

9. The storage tank of claim 8, wherein the vertical wall is attached to the riser.

10. The storage tank of claim 8, wherein a top of the sealing is positioned below a top of the riser.

11. The storage tank of claim 1, wherein the sealing dome has a circular circumferential shape.

12. The storage tank of claim 1, wherein the main body comprises a wastewater storage tank.

13. The storage tank of claim 1, wherein the fillet comprises putty.

14. The storage tank of claim 1, wherein the fillet comprises cardboard.

15. A storage tank comprising:
    a main body;
    a riser attached to the main body;
    a sealing dome covering an end of the riser, the sealing dome and the riser forming an overlapping joint;
    a circumferential fillet covering the joint, the fillet having a first surface adjacent to a portion of the sealing dome and a second surface adjacent to a portion of an exterior wall of the riser, the fillet comprising a material that will bond no more than weakly to the portion of the sealing dome and the portion of the riser;
    a sealing band formed over the fillet, the sealing band being attached to the sealing dome and the riser and forming an airtight seal between the sealing dome and the riser, the sealing band being comprised of fiberglass.

16. The storage tank of claim 15, wherein the sealing dome includes a flanged end sized to accept the riser and wherein the sealing dome is positioned with the flanged end over a top end of the riser.

17. The storage tank of claim 15, wherein the riser is comprised of fiberglass.

18. The storage tank of claim 15, wherein the sealing dome is comprised of fiberglass.

19. The storage tank of claim 15, wherein the sealing dome comprises a vertical wall and a top attached to an inside surface of the vertical wall.

20. The storage tank of claim 16, wherein the top includes a flat outer portion and a domed inner portion.

21. The storage tank of claim 16, wherein the vertical wall is attached to the riser.

22. The storage tank of claim 16, wherein a top of the sealing dome is positioned below a top of the riser.

23. The storage tank of claim 16, wherein the sealing dome has a circular circumferential shape.

24. The storage tank of claim 16, wherein the fillet comprises putty.

25. The storage tank of claim 16, wherein the fillet comprises cardboard.

26. The storage tank of claim 15, wherein the sealing band is adhered to the riser and to the sealing dome.

27. The storage tank of claim 15, wherein the fillet weakly adheres to the portion of the sealing dome and the portion of the riser.

28. The storage tank of claim 1, wherein the sealing band is adhered to the riser and to the sealing dome.

* * * * *